United States Patent
Ghosh et al.

(10) Patent No.: US 10,613,098 B2
(45) Date of Patent: Apr. 7, 2020

(54) SELECTIVE DETECTION AND ANALYSIS OF SMALL MOLECULES

(75) Inventors: Dipankar Ghosh, New Delhi (IN); Venkateswarlu Panchagnula, Maharashtra (IN); Deepika Dhaware, Maharashtra (IN)

(73) Assignees: Council of Scientific and Industrial Research, New Delhi (IN); Jawaharlal Nehru University, New Delhi (IN)

( * ) Notice: Subject to any disclaimer, the term of this patent is extended or adjusted under 35 U.S.C. 154(b) by 205 days.

(21) Appl. No.: 14/000,145

(22) PCT Filed: Feb. 17, 2012

(86) PCT No.: PCT/IN2012/000113
§ 371 (c)(1),
(2), (4) Date: Aug. 16, 2013

(87) PCT Pub. No.: WO2012/111028
PCT Pub. Date: Aug. 23, 2012

(65) Prior Publication Data
US 2013/0323849 A1    Dec. 5, 2013

(30) Foreign Application Priority Data
Feb. 17, 2011  (IN) .............................. 407/DEL/2011

(51) Int. Cl.
*G01N 33/68* (2006.01)
*H01J 49/04* (2006.01)
(Continued)

(52) U.S. Cl.
CPC ........ *G01N 33/6851* (2013.01); *B01J 20/103* (2013.01); *B01J 20/283* (2013.01);
(Continued)

(58) Field of Classification Search
CPC .. B01J 20/103; B01J 20/28083; B01J 20/283; B01J 20/3204; B01J 20/3236;
(Continued)

(56) References Cited

U.S. PATENT DOCUMENTS 6,958,480 B1    10/2005  Iyer et al.
2011/0318249 A1*  12/2011  Nakayama et al. .......... 423/325

FOREIGN PATENT DOCUMENTS

WO    WO 2010/088001 A2    8/2010

OTHER PUBLICATIONS

Chang-Soo Lee et al: "Analysis of small molecules by desorption/ionization on mesoporous silicate (DIOM)—mass spectrometry (MS)", Microporous and Mesoporous Materials, vol. 98, No. 1-3, Dec. 7, 2006 (Dec. 7, 2006) , pp. 200-207, XP005795677, ISSN: 1387-1811, DOI: 10.1016/J.MICROMESO.2006.09.005 the whole document.

(Continued)

*Primary Examiner* — Rebecca M Fritchman

(57) ABSTRACT

The invention relates to a material, process and method for the selective analysis of small molecules. Particularly the invention provides a material and a technique for the analysis of small molecules excluding other large molecular weight (MW) analytes. The process involves selective detection of low molecular weight molecules from a sample comprising the steps of placing said sample with SBA-15 particles; and subjecting the same to desorption ionization mass spectrometry, wherein low molecular weight molecules are selectively detected over the higher molecular weight molecules. A kit for the selective analysis of small molecules is also provided.

13 Claims, 12 Drawing Sheets

(51) Int. Cl.
*B01J 20/10* (2006.01)
*B01J 20/28* (2006.01)
*B01J 20/32* (2006.01)
*B01J 20/283* (2006.01)
*G01N 33/00* (2006.01)
*G01N 1/40* (2006.01)

(52) U.S. Cl.
CPC ... *B01J 20/28045* (2013.01); *B01J 20/28083* (2013.01); *B01J 20/3204* (2013.01); *B01J 20/3236* (2013.01); *H01J 49/0418* (2013.01); *G01N 1/405* (2013.01); *G01N 2560/00* (2013.01)

(58) Field of Classification Search
CPC .............. B01J 20/28045; G01N 1/405; G01N 33/6851; H01J 49/0418
USPC ...................................... 436/71, 90; 422/439
See application file for complete search history.

(56) References Cited

OTHER PUBLICATIONS

Xiuhua Li et al: "MALDI-TOF-MS analysis of small molecules using modified mesoporous material SBA-15 as assisted matrix", Journal of the American Society for Mass Spectrometry, vol. 20, No. 11, Nov. 1, 2009 (Nov. 1, 2009), pp. 2167-2173, XP026688364, ISSN: 1044-0305, DOI: 10.1016/J.JASMS.2009.08.003 [retrieved on Aug. 12, 2009] the whole document.

Chang-Soo Lee et al: II Laser desorption/ionization-mass spectrometry using mesoporous silicate as matrix for the analysis of various molecules, Biotechnology and Bioprocess Engineering, vol. 12, No. 2, Apr. 1, 2007 (Apr. 1, 2007), pp. 174-179, XP55035190, ISSN: 1226-8372, DOI: 10.1007/BF03028645 the whole document.

Rosa Terracciano et al: "Selective binding and enrichment for low-molecular weight biomarker molecules in human plasma after exposure to nanoporous silica particles". Proteomics, vol. 6. No. 11, Jan. 1, 2006 (Jan. 1, 2006), pp. 3243-3250, XP002414401, ISSN: 1615-9853. DOI: 10.1002/PMIC.200500614 cited in the application p. 3245, left-hand column, paragraph 6—p. 3247, left-hand column, paragraph 2 figures 1-5.

Thomas M. Annesley, "Ion Suppression in Mass Spectrometry", Clinical Chemistry, 2003, 49:7, 1041-1044.

Eberhard Krause, et al., "The Dominance of Arginine-Containing Peptides in MALDI-Derived Tryptic Mass Fingerprints of Proteins", Anal. Chem., 1999, 71, 4160-4165.

"MALDI-TOF Sample Preperation Guide", Jan. 30, 2008, google.com, https://www.google.com/url?sa=t&rct=j&q=&esrc=s&source=web&cd=4&cad=rja&uact=8&ved=2ahUKEwj9v4O5wPXiAhVTb30KHR0IAk8QFjADegQIBRAC8&url=https%3A%2F%2Fchemistry.mit.edu%2Fwp-content%2Fuploads%2F2018%2F08%2FDCIF-MALDI_sample_prep_0.pdf&usg=AOvVaw0pUVQkm_WaC26vcE8VVDGV.

Farzin Gharandaghi, et al., "Peptide-Mass Profiles of Polyvinylidene Difluoride-Bound Proteins by Matrix-Assisted Laser Desorption/Ionization Time-of-Flight Mass Spectrometry in the Presence of Nonionic Detergents1", Analytical Biochemistry, 1996, 233, 94-99., Article No. 0012.

J. L. Sterner, et al., "Signal suppression in electrospray ionization Fourier transform mass spectrometry of multi-component samples", J. Mass Spectrom., 2000, 35, 385-391.

\* cited by examiner

| Sr. No. | Quorum Sensing (QS) molecules | Bacteria producing the QS molecules | Exact Masses | |
|---|---|---|---|---|
| | | | $[M+H]^+$ | $[M+Li]^+$ |
| 1 | N-Tetradecanoyl-DL-Homoserine Lactone | *Acidithiobacillus ferrooxidans* | 312.2539 | 318.2620 |
| 2 | N-Dodecanoyl-DL-Homoserine Lactone | *Vibrio alginolyticans* | 284.2226 | 290.2307 |
| 3 | N-Decanoyl-DL-Homoserine Lactone | *Azospirillum lipoferum TW3* | 256.1913 | 262.1994 |
| 4 | N-Octanoyl-DL-Homoserine Lactone | *Yersinia enterolytica* | 228.1600 | 234.1681 |
| 5 | N-Heptanoyl-DL-Homoserine Lactone | *Rhizobium leguminosarum* by *viciae* | 214.1443 | 220.1525 |
| 6 | N-Hexanoyl-DL-Homoserine Lactone | *Pseudomonas aeruginosa* | 200.1287 | 206.1368 |
| 7 | N-Butyryl-DL-Homoserine Lactone | *Pseudomonas aeruginosa* | 172.0974 | 178.1055 |
| 8 | N-(β-Ketocaproyl)-DL-Homoserine Lactone | *Lactobacillus plantarum* | 214.1079 | 220.1161 |

Figure 3

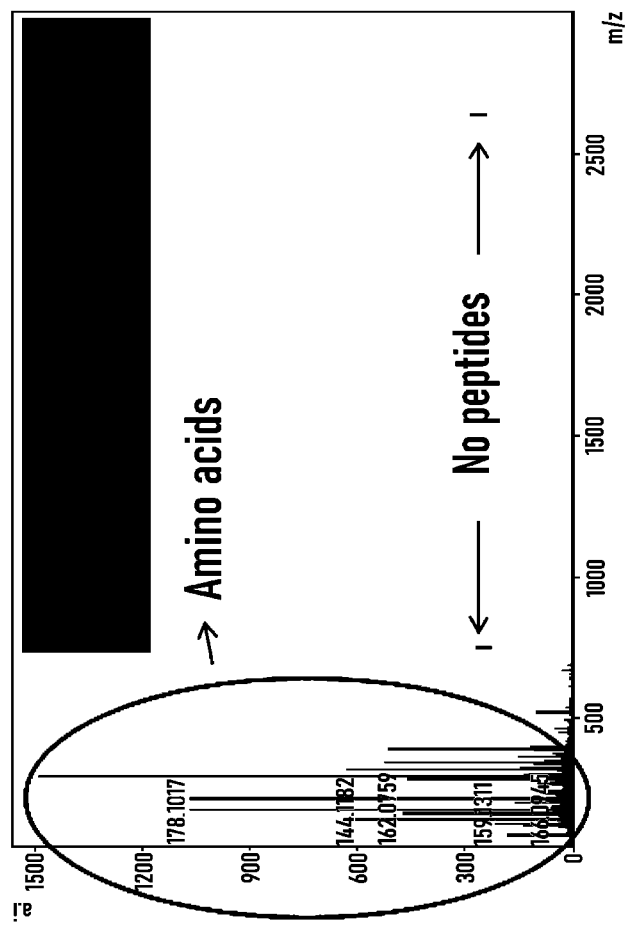
Figure 8 (contin.)

US 10,613,098 B2

SELECTIVE DETECTION AND ANALYSIS OF SMALL MOLECULES

RELATED APPLICATION INFORMATION

This application is a 371 of International Application PCT/IN2012/000113 filed 17 Feb. 2012 entitled "Selective Detection and Analysis of Small Molecules", which was published on 23 Aug. 2012, with International Publication Number WO2012/111028, and which claims priority from Indian Application No.: 407/DEL/2011 filed 17 Feb. 2011, the contents of which are incorporated herein by reference.

FIELD OF THE INVENTION

This invention relates to a material, process and method for the selective analysis of small molecules. Particularly the invention provides a material and a technique for the analysis of small molecules excluding other large molecular weight (MW) analytes.

BACKGROUND OF THE INVENTION

Analysis of biomolecules is a challenge due to the complex nature of biological samples. Most biological samples contain a diverse range of analytes with different biochemical functionalities, molecular sizes and masses as well as presence in varying abundances. Furthermore, these can also be present in various physical manifestations such as liquids, vapors/gaseous phases containing volatiles, solids and various forms of soft matter such as tissues, emulsions, networks, composites etc. Thus, maneuvering a given biological sample to analyze and understand the biochemical components present therein is an enormous task. Such information is of vital importance in healthcare/medical applications and numerous other commercial applications that are non medical/healthcare in nature.

One of the approaches followed in such situations is to study the sample profile and simplify it, but this may result in compromising the scope of the analysis. Also currently, separation, isolation and detection are performed separately moving from one platform to another severely compromising analytical performance.

'Matrix assisted laser desorption/ionization (MALDI) mass spectrometry' is a useful and popular analytical tool for large molecules such as peptides, polymers and proteins. However, due to inherent peaks from the 'matrix' that interfere in the low molecular region, MALDI is quite unpopular for small molecule analysis. In MALDI MS, all the analytes including the matrix itself are detected. Suspected ion suppression from the matrices has also been considered to be a major bottleneck for small molecule analysis using MALDI MS.

Laser desorption ionization mass spectrometry (LDI MS) is commonly referred to the techniques, which do not use organic matrices (unlike MALDI MS). The consequence of this is that smaller molecules which cannot be analyzed mass spectrometrically using MALDI MS can now be analyzed along with larger molecules such as peptides. It must be emphasized that all the prior art using LDI or MALDI describe analysis of both small and large molecular weight analytes and none of these refer or imply "preferential" or "selective" analysis over the other classes of analytes. Thus prior art on LDI MS even if illustrating small molecule analysis do not make any reference to "selectivity" or "preference" over the rest of the molecules and quite often demonstrate the larger utility of LDI for both smaller and larger molecular weight analytes. A few specific examples of the prior art are detailed below in this regard.

To overcome the limitations and disadvantages of MALDI MS, a wide range of materials have been demonstrated for use as alternatives to the organic matrices in LDI MS. These include polymers, surfactants, activated carbon, carbon nanotubes and inorganic materials (like germanium nanodots (Seino, 2007 #33), platinum nanoflowers (Kawasaki, Yonezawa et al. 2007), metal oxide nanoparticles (Kinumi, Saisu et al. 2000), silicon nanowires (Go, Apon et al. 2005), metal oxide porous films (Chen and Chen 2004) etc.). The use of metal oxide particles and films being the most preferred as one could perform a 'matrix-free' analysis in real sense by removing/reducing the contribution from the matrix in the small molecule region (m/z<700).

One example of 'matrix-free' analysis is porous silicon (not silica), popularly known as DIOS (desorption ionization on porous silicon), which was investigated for its use in mass spectrometry as an alternative to MALDI MS. Wafers of silicon were produced and commercialized as 'DIOS target plates' for the analysis of proteins, peptides and many other analytes using laser desorption/ionization mass spectrometry (Siuzdak, Buriak et al. 2000) (Wei, Buriak et al. 1999) (Shen, Thomas et al. 2001) (Thomas, Shen et al. 2001). It is believed that the silicon wafer "softly" transmits the UV laser energy to the analytes leading to their desorption and ionization followed by mass spectral identification, usually in a 'time-of-flight' tube where analytes traveling in a tube with applied electrical potential get separated by virtue of their mass by charge ratios (m/z). This material and the method is universal and does not discriminate or offer selectivity between various types of analytes. The primary objective of this prior art is to provide an alternative to MALDI MS. Thus in this example described DIOS enables the detection of small as well as large MW analyte detection minus the 'matrix' interference.

U.S. Pat. No. 6,958,480 claims a method of performing 'matrix-free' laser desorption/ionization mass spectrometry using a nanocomposite comprising mesoporous silica thin film on porous silicon, glass etc. This composite film is prepared by dispersing a silica precursor (tetraethyl orthosilicate TEOS) in a surfactant solution that is spread on yet another material, a silica wafer or a glass slide in this embodiment, to make it into a composite material in the form of a thin film. The final nanocomposite thin film is obtained by removing the surfactant employed as a template by means of exposing the films to deep UV light or by calcination at elevated temperatures. An analyte is then placed on this composite thin film, which is subsequently subjected to laser desorption/ionization mass spectrometry as described above. The thickness of the film is in the range of 70-300 nm with pore sizes of 1-50 nm. This nanocomposite film presents better performance characteristics over the above mentioned DIOS plates, but is used essentially for the same purpose of universally analyzing samples. Its advantage is as a superior method relative to the traditional MALDI MS. Thus, this nanocomposite based mesoporous technology also enables the detection of small as well as large MW analytes in a given sample minus any interference from the matrix. The invention does not disclose any selective analysis or ionization resulting from the material or the method. The inventors in the above mentioned patent also disclosed that peptides such as Angiotensin II, Bradykinin 1-7, P14R and ACTH 18-39 fragments were detected using this method wherein LDI MS was performed by placing a sample on the nanocomposite (Dattelbaum, Hicks et al. 2008). An article titled "Mesoporous silica for Desorption- Ionization Mass Spectrometry" by the same authors A. Dattelbaum et al published in Nanotech, Vol. 1, Ch. 5, pages 225-228, 2005. (Srinivas Iyer and Andrew M. Dattelbaum 2005) discloses use of mesoporous silica thin film nanocomposites for mass spectrometric analysis of both tryptophan (lower m/z) and angiotensin (peptide).

It is also noteworthy that "porous silicon" wafer alone is already covered as a patent by another group for its utility in LDI MS (no selectivity has ever been covered) that is termed as DIOS as detailed in line numbers 51 to 60 (Siuzdak et. al.). Despite this, the combination of porous silicon and mesoporous silica has been granted a patent for the same utility, which is LDI MS (U.S. Pat. No. 6,958,480).

In summary, large MW analytes can only be analyzed in the LDI MS mode using either the "organic matrix" such as 2,5-dihydroxybenzoic acid (DHB) and α-cyano hydroxy cinnamic acid α-CHCA) or the "porous silicon wafer" or "a nanocomposite thin film comprising mesoporous silica" or a few other materials.

An article titled "Selective binding and enrichment for low-molecular weight biomarker molecules in human plasma after exposure to nanoporous silica particles" by Rosa Terracciano, e.t al. published in Proteomics, Volume 6 Issue 11, pg 3243-3250, 2006, having DOI 10.1002/pmic.200500614. US 2008/0277578 A1 discloses biomarker capturing strategy based on nanoporous silica particles. The strategy as described herein comprises of exposing a plasma sample to a silica particle thereby enriching low molecular weight biomolecules (m/z 800-10,000) that are peptides and proteins followed by a separate MALDI-MS analysis of the biomolecules extracted from the silica using conventional matrices like α-cyano hydroxy cinnamic acid (α-CHCA). In this document the definition of low molecular weight molecules includes analytes molecular weight range 800 to 10,000. In this document silica porous particles (not to be mistaken with mesoporous SBA-15 prepared using template assisted synthesis) or beads are used for ONLY enrichment. Analytes are then removed for conventional MALDI MS using various matrices such as α-CHCA. It is noteworthy that various methods exist for enrichment of various classes of molecules that operate without a concurrent mass spectral dimension. A case in point is the TiO2 enrichment of phosphopeptides that is a commercial product with extensive prior art. Also, the porous silica used has non uniform pore size and not as well defined as SBA-15, The document enriches peptides and proteins with m/z 800-10,000.

The present invention/method involves selective exclusion of these peptides and proteins and detecting only the smaller analytes (MW typically less than 1000 Da). This is achieved in the present invention by a material SBA-15, which enables desorption and mass spectral analysis of small molecules from mixtures containing large analytes. Signals for the small molecule analytes are obtained directly from the material itself without the addition of an external matrix.

In summary, there is no prior art on a material, process or method using mesoporous SBA-15 that can be used for the selective mass spectrometric determination of small molecular weight (typically less than 1000 m/z) analytes while excluding large molecular weight analytes in complex mixtures.

Therefore, a quick-yet selective material and method involving minimal or no sample preparation, labeled or label-free detection that enables simultaneous mass spectral analysis is an extremely valuable tool. Such tool is significantly benefit research in biological, chemical and related sciences. Such a material and method finds wide applicability in diverse areas such as drug discovery research, proteomics, metabolomics, and in general any other application where an efficient analytical solution is needed.

With the miniaturization of mass spectrometers (Shimma S., et. al. Analytical Chemistry 2010, 82, 8456; Ouyang, Z. et. al., Analytical Chemistry 2009, 81, 2421; Kissinger, P. T. et. al., http://www.ivdtechnologv.com/article/developing-point-care-mass-spectrometer), and potential use of these instruments at point of care and point of action (such as hospitals, airports, defense applications), it is also imperative that a material enabling a method and process to selectively detect, distinguish and identify analytes of interest would be of enormous utility and commercial as well as societal importance.

The invention described herein involves (a) a process/product using pure porous material that is distinct from the prior art using various other materials or various physical forms and (b) leading to a unique utility not covered by the prior art (selective or preferential mass spectral detection of low MW molecules that are not peptides or proteins; not just LDI MS or enrichment of peptides as in the prior art).

OBJECT OF THE INVENTION

Therefore, an object of the present invention is to provide a process for the selective analysis of small molecules.

Another object of the invention is to provide a material for the selective detection of small molecules.

Yet another object of the invention is to develop a kit for the selective detection of small molecules excluding large molecular weight analytes in complex mixtures.

BRIEF DESCRIPTION OF DRAWINGS

FIG. 3. Exact masses of the protonated and cationized adducts of the N-Acyl homoserine lactones used for the analysis. The molecules under study show affinity towards cationization over protonation and hence the molecules were subjected to complete cationization to improve the sensitivity of the analysis and to restrict the number of adducts formed.

SUMMARY OF THE INVENTION

Figure 1:
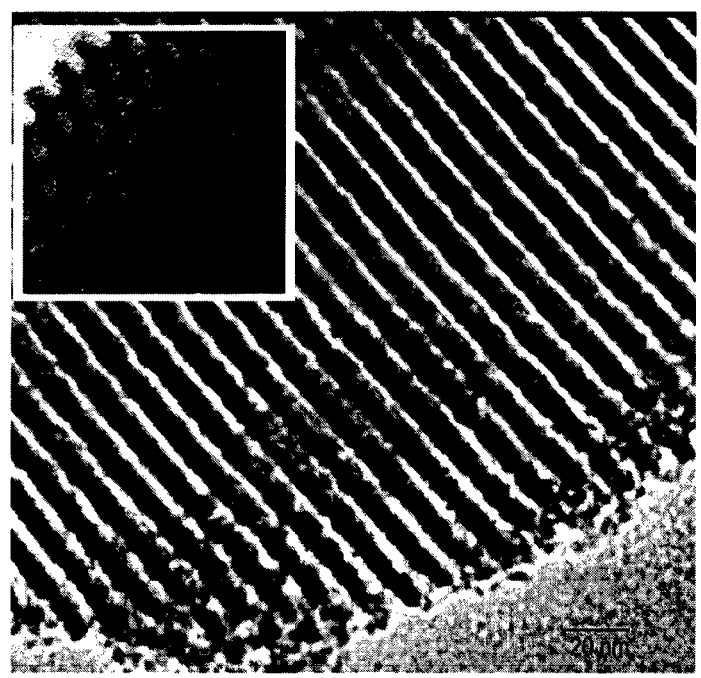
FIG. 1. Transmission electron microscopy (TEM) image of the synthesized mesoporous silica, SBA-15 particles showing a honeycomb structure and an average pore size of about 8 nm. The pore size was confirmed with N2 adsorption studies.

This invention provides a material, process and method for the selective analysis of small molecules. Particularly the invention provides a material and a technique for the analysis of small molecules excluding other large molecular weight (MW) analytes.

In one embodiment, the invention provides a process for the selective detection of low molecular weight molecules from a sample comprising the steps of placing said sample with SBA-15 particles; and subjecting the same to desorption ionization mass spectrometry, wherein low molecular weight molecules are selectively detected over the higher molecular weight molecules.

In another embodiment, wherein SBA-15 or sample are present in a solvent system. The solvent system is selected from organic solvents such as methanol, acetonitrile and ethyl acetate. In preferred embodiment SBA-15 and methanol are present in ratio of 5:1 (w/v).

In another embodiment, either SBA-15 and/or the sample are chemically or physically modified. In another embodiment, the said modifier is a chemical or physical agent that introduces positive or negative charges to low molecular weight analytes to improve their selective mass spectrometric analysis.

In another embodiment, sample to be detected is used with the modifiers that modify the charge present on the surface of molecules to be detected. To introduce positive charge, the said modifiers are selected from alkali metal salts. In the preferred embodiment said modifier is lithium chloride. The modifiers are present in a ratio ranging from 1:1-7:1 (w/v) with SBA-15.

In yet-another embodiment, the modifier enables sensitive detection and MS/MS analysis.

In another embodiment the molecules detected have molecular weight less than 1000 (m/z).

In another embodiment the sample detected is a fluid of biological or synthetic origin comprising a mixture of small molecular weight analytes and large molecular weight analytes. The said sample could also be a solid, semi solid, gel, amorphous mixture, or a surface of biological or synthetic origin comprising a mixture of small molecular weight analytes and large molecular weight analytes. In preferred embodiment the molecules detected are selected from bacterial quorum sensing molecules, amino acids, synthetic or modified small molecules, lipids, fatty acids and their derivatives, therapeutic, pharmaceutical and drug molecules, metabolites, food, pesticide and environmental samples.

In another embodiment, wherein the said material and process will be used for clinical diagnostics, forensics, dope and narcotic analysis, environmental analysis, microbial community analysis and quorum sensing, pesticide analysis, food analysis, industrial fermentation, active pharmaceutical ingredient (API) or drug discovery or for high throughput mass spectrometry research use and practice wherein the samples comprise a mixture of small molecular weight analytes and large molecular weight analytes.

In another embodiment, the detection of small molecules involves minimal, optimal or no sample preparation.

In another embodiment, SBA-15 particles are employed as particles as powder or suspension in reagents or on a surface or as a free standing film or as a part of a device such as a chromatographic or mass spectrometric surface or device.

In another embodiment the invention provides a process of performing selective laser desorption ionization mass spectrometry comprising preparing mesoporous SBA-15 particles having a desired pore size by preparing a suspension of SBA-15 particles in a solvent system selected from organic solvents preferably methanol optionally subjecting solution of step a to sonication dispersing SBA-15 in a solvent system comprising triflouoroacetic acid (TFA), mixing said suspension of SBA-15 with a sample of analytes/molecules, subjecting the solution of previous step to a laser in an ion generating section of a mass spectrometer to desorb and ionize the sample; and detecting the desorbed and ionized sample. In further embodiment sample to be detected is modified with the charge modifiers. In another embodiment the ratio of SBA and TFA is 1:1 [v/w].

In another embodiment is provided a chemically modified SBA-15.

In another embodiment is provided use of SBA-15 modified or unmodified for the detection of low molecular weight molecules (less than 1000 m/z) while excluding molecules of molecular weight 1000 (m/z) or above.

In yet another embodiment is provided a kit for the detection of small molecules from a complex mixture of analytes comprising first part consisting of SBA-15 and second part containing chemical reagents, wherein said SBA-15 is in the form of a powder or suspension in reagents or on a surface or as a free standing film or as a part of a device such as a chromatographic or mass spectrometric surface or device. In another embodiment the first part consists of SBA-15 powder in methanol in a ratio of 5:1 (w/v). In further embodiment, in said kit is provided a third tube consisting of charge modifiers. In another embodiment said kit comprises SBA-15 layered with a charge modifier.

In further embodiment kit comprises a tube consisting of standard compounds.

In another embodiment kit also comprises a surface for spotting the sample. The surface is a steel multi well plate. In another said kit SBA-15 is coated on a surface.

In another embodiment the invention provides a process of selective detection of small molecules from a sample comprising complex sample of molecules using a kit comprising the steps of preparing a solution of sample to be detected by mixing said sample with the reagents of second tube in a ratio of 1:1, mixing the two solutions, spotting said solution on the surface provided in the kit and subjecting the same to laser desorption ionization mass spectrometry.

DETAILED DESCRIPTION OF THE INVENTION

The present invention provides a material, process and method for the selective detection and analysis or estimation of small molecules over larger molecules. In particular the invention provides selective laser desorption/ionization mass spectrometric determination of small molecular weight molecules while excluding high molecular weight molecules from a mixture comprising high molecular weight and low molecular weight analytes/molecules.

The analytes to be analysed are present originate from a biological source or are from a synthetic source containing small and larger molecules. The complex sample mixture is analyzed using the process and method described before. The process excludes detection of high MW molecules such as proteins and peptides and such like that are detected by conventional mass spectrometric techniques. The process selectively detects and analyse low molecular weight molecules using appropriately prepared mesoporous SBA-15 embodiments.

The invention also provides preparation of mesoporous SBA-15 particles. A variety of methods are employed for the synthesis of mesoporous materials such as SBA-15. The choice of template/polymer/surfactant depends on the characteristics desired like the pore size and overall morphology of the particles formed. Varying the process of synthesis can thus provide one with materials with different structural morphology, which can yield a similar and/or desired selectivity or exclusion.

The mesoporous SBA-15 particles are prepared in a particular solvent system such as methanol or acetonitrile (ACN) or ethyl acetate and sonicated well to disperse the same. The solvent systems used to disperse the SBA-15 particles can contain a 0.1% trifluoroacetic acid (TFA) (50:50 v/v).

The SBA-15 particles are employed as particles as powder or suspension in reagents or on a surface or as a free standing film or as a part of a device such as a chromatographic or mass spectrometric surface or device. The SBA-15 may be present as a coating on a surface for detection of molecules. Time for drying of the SBA-15 coating 1 to 5 min at 25 degrees C. and air drying. The activation of SBA-15 by physical and chemical treatments also improves performance features such as sensitivity. The activation of SBA-15 may be done by either of the steps: Laser induced activation under high vacuum conditions, Microwave induced activation, Thermal activation using heating under controlled conditions, and other chemical or physical induced treatments for activation and enhanced analytical performance.

In one aspect mesoporous SBA-15 particles are chemically modified or a modifier is used in accordance with the sample to be detected to ensure selectivity towards a particular class or group of analytes.

Figure 8:
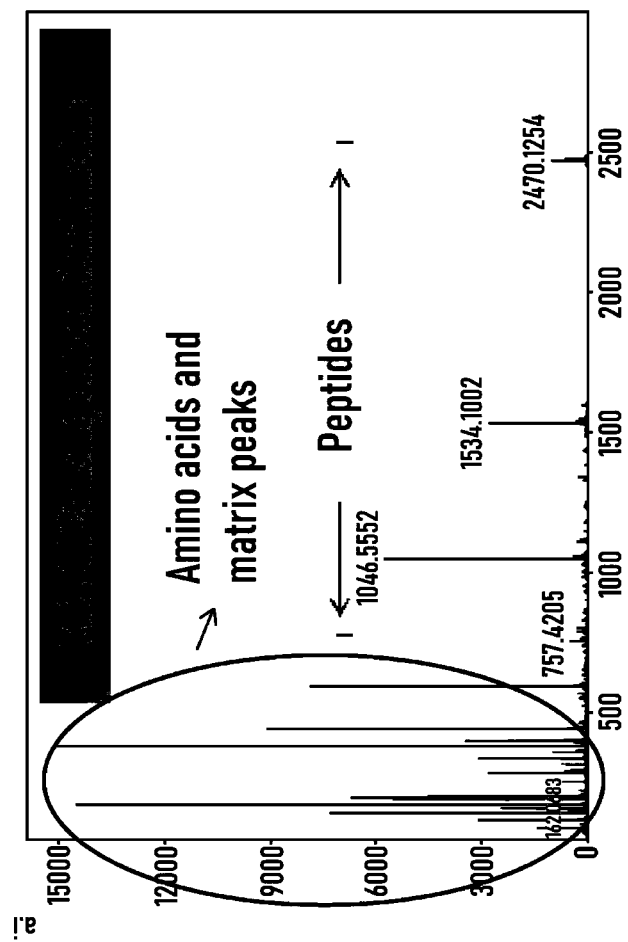
FIG. 8: Detection of amino acids using conventional MALDI MS and LDI MS on SBA-15.

The following are examples of process and chemical modifications performed:

(1) Addition of lithium chloride in methanol (7.5 mg/mL) to the suspension of SBA-15 in methanol enabled selective mass spectral detection of amino acids in the presence of peptides from a test mixture containing both. The following amino acids present in the test mixture with their lithiated adducts that were selectively detected: leucine (1144.1117), isoleucine (144.1117), valine (130.0986), tyrosine (194.0905), tryptophan (217.1066), phenylalanine (178.0944), methionine (162.0683), lysine (159.1246), while the peptides bradykinin 1-7, angiotensin II, P14R and ACTH 18-39 [m/z 757.4075, 1056.5511, 1533.866, 2465.2067 respectively] were selectively excluded. Without the addition of lithium chloride, amino acids were not detected at all [FIG. 8]

(2) Addition of lithium chloride (7.5 mg/mL) to the suspension of SBA-15 in methanol for N-acyl homoserine lactones followed by the above described process of detection selectively yielded only lithiated adducts in the mass spectra. Without lithiation, numerous adducts such as protonated, sodiated, and potassiated were formed complicating the spectra leading to poor resolution, sensitivity and detection of the analytes.

(3) SBA-15 was also chemically modified to introduce a light absorbing moiety, such as ($\alpha$) alpha-CHCA into the mesopores with an aim to eliminate selectivity and to show that selectivity can be tuned with chemical modification. The chemical modification was performed by attaching covalently a silylated amine such as 3-amino propyl triethoxy silane (200 uL, 1 mmol) to the free silanol groups on SBA-15 and then this so formed ionic precursor was reacted with the anion of the standard MALDI matrices like alpha-cyano-4-hydroxy cinnamic acid (alpha ($\alpha$)-CHCA; 119 mg, 1 mmol) followed by thorough workup and cleaning to remove any adsorbed alpha-CHCA. This formed an ionic macro complex which was used further for the LDI-MS studies. The insertion of alpha-CHCA into the mesoporous structure of SBA-15 was characterized using IR spectroscopy, SEM and TEM. IR spectroscopy indicated the amine functionalization and TEM indicated the porosity expected of the SBA-15 materials. Absence of alpha-CHCA crystals in the SEM images indicated that the alpha-CHCA was inserted into the pore. It is also noteworthy that the SEM images of modified and unmodified SBA-15 were similar (FIG. 9 indicating that their function was determined only by either the presence or absence of alpha CHCA.

Figure 10:
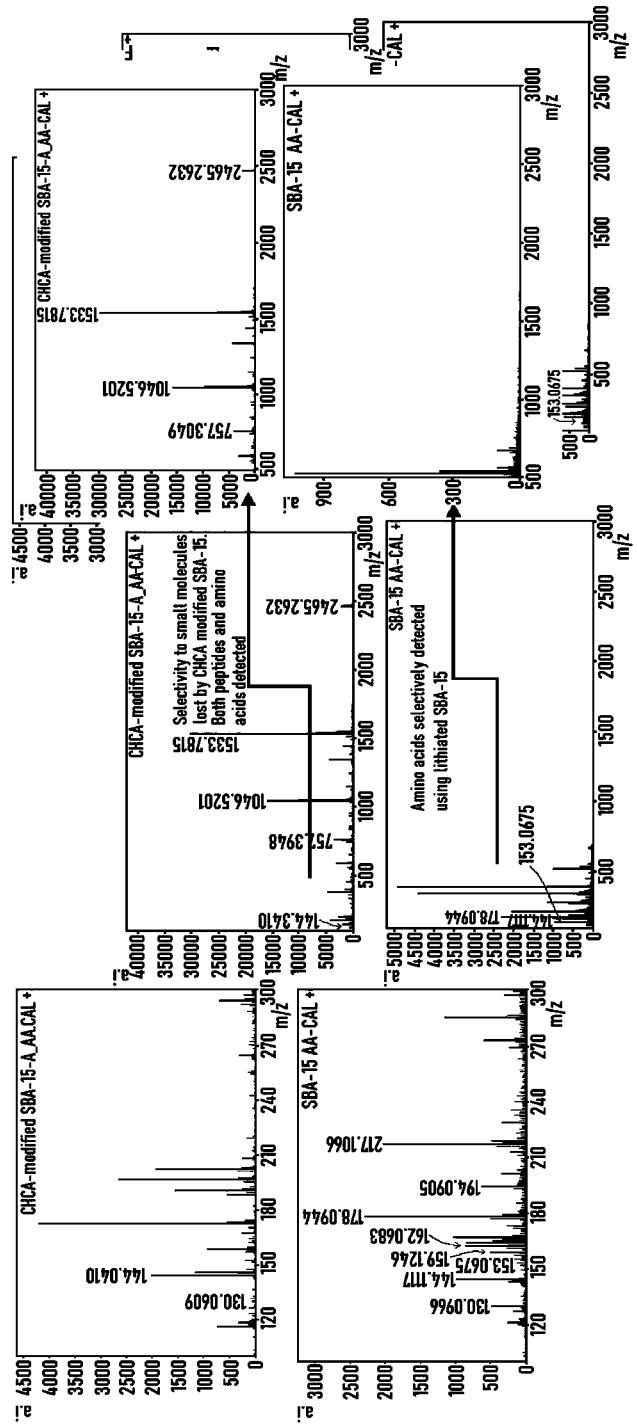
FIG. 10: Detection of peptides and amino acids using SBA-15 modified with light absorbing moiety.

With this modification, a mixture of amino acids and peptides mentioned earlier in this document were tested. Peptides hitherto excluded were detected in high mass spectral intensities clearly showing that the selectivity towards small molecules was lost, while the amino acid signal was being interfered by some of the alpha-CHCA peaks. This example proves two concepts. Firstly, it shows evidence that the SBA-15 can be modified to tune the selectivity. Secondly, this result demonstrates the basis of selectivity. A light absorbing moiety such as alpha-CHCA absorbs the laser energy and utilizes it towards universal analyte desorption and ionization. In the absence of any such light absorbing moiety, SBA-15 excludes the larger molecules from getting desorbed and ionized for mass analysis, while the available thermal energy is sufficient for smaller molecules to undergo desorption, ionization and mass spectral detection. [FIG. 10]

Figure 9:
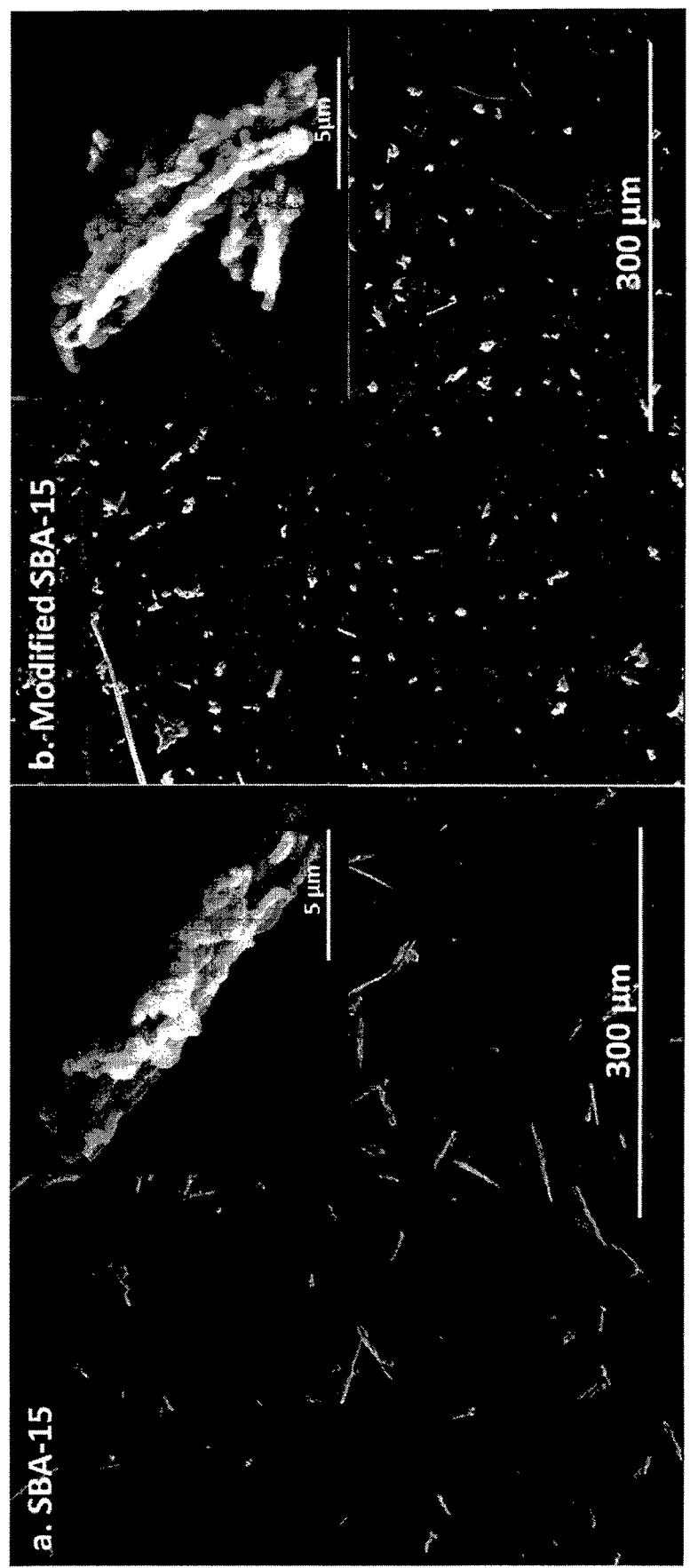
FIG. 9: SEM images of a) SBA-15 and b) SBA-15 modified with alpha (α)-CHCA.

FIG. 9 reveals that the introduction of a light absorbing moiety such as alpha($\alpha$)-CHCA that is routinely used as MALDI matrix, into the porous structure of the SBA-15, selective detection of small molecules was lost. Peptides, hitherto undetected using unmodified SBA-15 suspension (bottom frame), were now detected in very high mass spectral signal intensities as can be seen from the above spectra clearly demonstrating a loss of selectivity towards smaller molecules (top frame). In addition to demonstrating tuning of selectivity through chemical modification, this experiment also confirms that the absence of a light absorbing chemical structure as the basis for selective small molecule detection with the SBA-15. A test mixture of amino acids and four peptide standards were used in this experiment. Using SBA-15 alone, the amino acids selectively detected as shown in the spectra above were: leucine (144.1117), isoleucine (144.1117), valine (130.0986), tyrosine (194.0905), tryptophan (217.1066), phenylalanine (178.0944), methionine (162.0683), lysine (159.1246). With CHCA modified SBA-15, all the four peptides that were previously selectively excluded were now detected due to the loss of selectivity (bradykinin 1-7, angiotensin II, P14R and ACTH 18-39, m/z 757.4075, 1056.5511, 1533.866, 2465.2067 respectively]. Furthermore due to the interference with CHCA peaks, only three amino acids (leucine (144.1117), isoleucine (144.1117) and valine (130.0986)) were only detected from the mix with CHCA modified SBA-15. The remaining amino acid peaks were either getting suppressed or not detected in the modified SBA-15 due to matrix interference.

The lower molecular weight analytes include but is not limited to (a) Bacterial quorum sensing molecules (b) Amino acids (c) Synthetic or modified small molecules (d) Lipids, fatty acids and their derivatives (e). Therapeutic, pharmaceutical and drug molecules (f) metabolites (g) food, pesticide and environmental and such similar lower molecular weight analytes.

The following are the examples of molecules that have been selectively detected using the material, process and method described in this invention: Amino acids such as leucine, isoleucine, valine, tyrosine, tryptophan, phenylalanine, arginine, histidine, methionine, lysine, serine, proline ([M−H+2Li], m/z 144.1117, 144.1117, 130.0986, 194.0905, 217.1066, 178.0949, 187.1325, 168.1013, 159.1246, 162.0683, 118.0567, 128.0834 respectively) and modified amino acids such as ornithine ([M−H+2Li] m/z 139.1042), hydroxyproline ([M−H+2Li], m/z 144.0812), phenylglycine ([M+Li], m/z 164.0823), symmetric dimethyl arginine ([M+H] m/z 203.1508), asymmetric dimethyl arginine ([M+H] m/z 203.1508), lipids and fatty acids and/or their esterified derivatives such as nervonic acid methyl ester, lignoceric acid methyl ester, tricosanoic acid methyl ester, cis-13, 16-docosadienoic acid methyl ester, erucic acid methyl ester, behenic acid methyl ester, heneicosanoic acid methyl ester, cis-5, 8, 11, 14, 17-eicosapentaenoic acid methyl ester, gamma linoleic acid methyl ester, linoleic acid methyl ester, myristoleic acid methyl ester, lauric acid methyl ester, undecanoic acid methyl ester, capric acid methyl ester, caproic acid methyl ester, butyric acid methyl ester ([M+Li] m/z 387.3810, 389.3923, 375.3856, 357.3324, 359.3495, 361.3628, 347.3495, 329.2624 (M−H+2Li), 299.2562, 305.2614 (M−H+2Li), 247.2229, 249.2400, 221.2075, 207.1923, 193.178, 137.1154, 115.0983 (M−H+2Li) respectively); N-acyl homoserine lactones class of bacterial sensing molecules, triglycerides (or their esters) such as: tripalmitin ([M+Li], m/z 813.7601), glyceryl tridodecanoate ([M+Li], m/z 645.5756), glyceryl tridecanoate ([M+Li], m/z 561.4822), glyceryl trioctanoate ([M+Li], m/z 477.3811), glyceryl trimyristate ([M+Li], m/z 729.6661); carbohydrates such as glucose ([M+Li], m/z 187.0825), fructose ([M+Li], 187.0825), lactose ([M+Li], n/z 349.1424), galactose ([M+Li], m/z 349.1424); sucrose ([M+Li], 349.1424) heterocyclic compounds such as mixtures of triazines 2,4-diamino-1,3,5-triazine, 2,4-diamino-6-methyl-1,3,5triazine, 2,4-diamino-6-(2-fluorophenyl)-1,3,5triazine, 2,4-diamino-6-(4-methoxyphenyl)-1,3,5 triazine ([M+H] m/z 112.0623, 126.0753, 206.0830, 218.1013 respectively); pharmaceutical and drug molecules such as verapamil ([M+Li], m/z 461.2912), ibuprofen ([M+Li], m/z 213.1440), griseofulvin ([M+Li], m/z 359.0718), acetaminophen (paracetamol) (158.0789); urea cycle metabolites and renal biomarkers such as creatinine, ornithinine, arginine, uracil, citrulline, ([M−H+2Li], m/z 126.0783, 139.1042, 187.1348, 125.0525, 188.1111 respectively); cardiovascular metabolites such as symmetric ([M+H] m/z 203.1508) and asymmetric dimethyl arginine ([M+H] m/z 203.1508); metabolites implicated in early. detection of diabetes: Leucine/isoleucine, valine, phenyl alanine and tryptophan, other bacterial and microbial metabolites; metabolites routinely used in new born, neo-natal, pre and post natal screening investigations such as phenylalanine, tyrosine, arginine, clinical samples and such like.

The present process of detection or analysis requires optimal, minimal or no sample preparation. Example of minimal sample preparation include extraction of the small molecules from complex samples into suitable solvent followed by selective detection using the process described herein. Example of no sample preparation include direct usage of complex samples from their biological matrices such as plasma, serum, urine, fluids, cultures followed by the selective detection as described above. Example of optimal sample preparation are wherein the above biological samples are made to interact over a predetermined time duration with the materials in the above described process and method.

A standard sample test mixture is prepared by mixing low molecular weight analytes for e.g. amino acids or lipids or N-acyl homoserine lactones and high molecule analytes for e.g. peptides or proteins in a solvent ideally compatible for all the analytes like ACN:TFA (0.1%) or methanol: (0.1%) TFA. In one aspect the standard sample test mixture containing low molecular weight analytes is treated with an alkali metal salt such as lithium chloride to generate cationized adducts.

The sample mixture to be analysed can also be a complex biological mixture or an extract thereof in an organic solvent such as ethyl acetate etc. or can be a synthetic impure mixture containing both low and high molecular weight analytes.

The present invention provides a process for the selective detection and analysis or estimation of small molecules over larger molecules. In particular the invention provides selective laser desorption/ionization mass spectrometric determination of small molecular weight biomolecules while excluding high molecular weight analytes from a mixture comprising high MW and low MW analytes.

In accordance with the objectives of the invention, a process of selective detection and analysis or estimation of small molecules using mesoporous SBA-15 particles is disclosed herein. Other modes of mass analysis including various other ionization sources as well as mass analyzers/detectors or a combination thereof along with other embodiments of sample preparation can also be used in conjunction with the SBA-15 particles for selective detection of low molecular weight analytes and/or selective exclusion of large molecular weight analytes such as peptides and proteins or for SLDI.

The invention also provides a kit comprising SBA-15 for the selective mass analysis. In one embodiment with different embodiments: In one embodiment, the kit would comprise of a tube with the unique suspension containing a predetermined concentration of (5:1, w/v) SBA-15 powder in methanol. A sample mixture to be analyzed is prepared having reagents such as ethyl acetate, acetonitrile, trifluoroacetic acid, methanol and standard compounds. Contents from the unique suspension as described above were mixed in a 1:1 ratio (or a similar ratio). The analytes and the unique suspension are made to interact for a predetermined duration with the contents of the suspension. In one embodiment such as analysis of the examples mentioned, the duration was less than a minute. However this duration of interaction can also be tailored differently to enable specific tasks namely: adsorption, concentration, storage and transport of time and environment sensitive as well as labile analytes in liquid solution. The latter is applicable for sensitive and point-ofcare applications such as microbial samples, clinical samples, diagnostics samples, bio terrorism agents, volatile matter and explosives.

In another embodiment kit comprises powder of SBA-15 to which samples of interest are added followed by selective mass analysis. In another embodiment SBA-15 is in the form of a free standing thin film. In another embodiment kit comprises a coating of the SBA-15 suspension on a predetermined surface such as a glass, quartz, fused silica, ceramic or a stainless steel surface. To this surface coating, a sample of interest is added followed by selective mass analysis. Such a coating can also be present on other materials for example gold, platinum, copper surface or an alloy made of these or other metals or a surface made of non metals.

Another embodiment of the kit comprises of SBA-15 with physical or chemical modifiers such as lithium chloride in suspension. To this mixture of SBA-15 and modifier, analytes or samples of interest are added followed by selective mass analysis.

Other manifestations include the modifications such as lithium chloride mixed in the SBA-15 powder or in a free standing SBA-15 film or lithium chloride and SBA-15 in methanol coated on a surface described above. A separate set of necessary reagents or standards will also be part of the kit.

In yet another embodiment, SBA-15 is mixed with a modifier of predefined ratio such as 1:2 (w/w) to introduce-charges (positive or negative depending on the modifier) to low molecular weight non polar analytes for enabling selective mass analysis.

In yet another embodiment, SBA-15 is mixed with lithium chloride in methanol (7:1 w/v) results in selective lithiation over sodiated and potassiated adducts of quorum sensing molecules like homoserine lactones, autoinducer peptides and others from bacterial biofilm cultures in synthetic media or biological fluids. The lithiated quorum sensing molecules exhibit higher signal to noise ratio enabling MS and MS/MS analysis.

In yet another embodiment the kit comprises of SBA-15 with or without sequentially layered modifier such a lithium chloride in a predetermined ratio such as 1:2 (w/w) that is exposed to sample of interest. A sample of interest can be aspirated through physical suction or passed through a cartridge containing the sequentially layered materials followed by selective mass analysis from SBA-15.

In still another significant embodiment, SBA-15 in its manifestations described above when placed on a sample surface ablates the surface layers enabling their transition into vapor or gaseous phase followed by selective mass analysis. This can also be achieved by placing the sample on top of the SBA-15 for mass analysis.

In each of the kit embodiments specified, SBA-15 storage is ensured.

The present invention is described with reference to the figures and examples, which are explained by way of illustration only and should not be construed to limit the scope of the present invention.

Example 1

Synthesis of Mesoporous SBA-15 Particles:

Synthesis of SBA-15 particles: The procedure was similar as given by (Zhao, Yang et al. 1998) with a few modifications as described below. 4 g of Pluronic-P123 (tradename, as marketed by BASF) was dissolved in 30 ml water and stirred vigorously for 4 hrs followed by addition of 120 ml (2N) HCl and stirred at 25*C, 1 h. The temperature of the stirring mixture was then increased to 40° C. and maintained for 1 h, 9 g Tetraethyl orthosilicate TEOS was added to this warm mixture dropwise. The mixture was then allowed to stir for 24 h at 40° C. This synthesised gel was then transferred and sealed in a bottle and allowed to age at 100° C. for 48 hr. The as-synthesized particles were then filtered and washed with DI water until neutral, air-dried and then calcined at 500° C. for 6 h at a heating rate of 1° C./min.

Example 2

Figure 2:
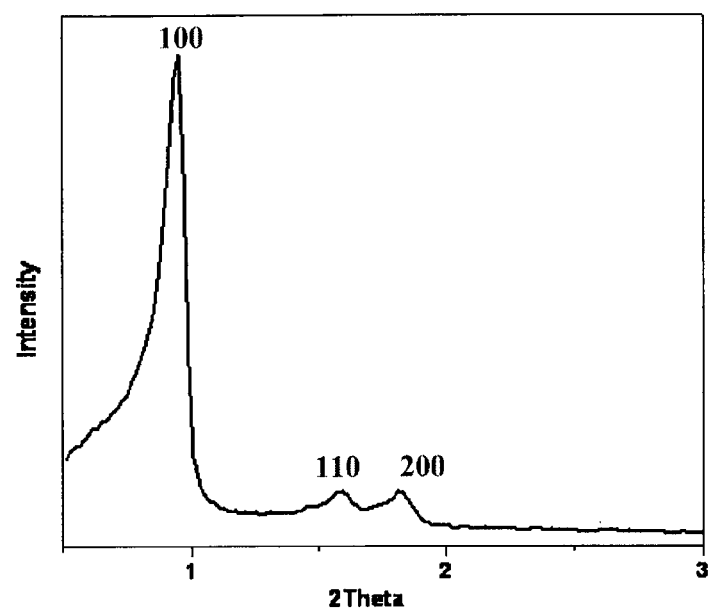
FIG. 2. Powder-XRD pattern of mesoporous SBA-15. The peak at 100 corresponding to the 2θ value 1° is a characteristic peak of SBA-15. Other peaks at 1100 and 200° indicate the formation of a well ordered one dimensional hexagonal mesoporous channels.

Characterization of Mesoporous SBA-15:

Powder XRD patterns for SBA-15 were collected on PANalytical X'pert Pro dual goniometer diffractometer equipped with a Cu Kα (1.5418 Å) radiation source with a Ni filter. For low angle measurements, a proportional counter detector was used and care was taken that no sample displacement occurred. Data was collected using a flat holder in Bragg-Brentano geometry (0.5 to 5; $0.2°min^{-1}$). Powder XRD pattern of calcined SBA-15 is shown in FIG. 2. The peak at 100 corresponding to the 2θ value 10 is a characteristic peak of SBA-15. Other peaks at 110° and 200° indicate the formation of a well ordered one dimensional hexagonal mesoporous channels. TEM images as shown in FIG. 2 clearly indicate the hexagonal arrangement of the pores and the formation of continuous long channels in a parallel fashion as reported elsewhere for mesoporous materials. The $N_2$-adsorption-desorption isotherms showed the characteristic Type IV isotherm pattern, which is indicative of mesoporosity and the pore size is 7.15 nm as calculated using BJH pore size model.

Example 3

Laser Desorption Ionization Mass Spectrometry (LDI MS) from SBA-15:

LDI MS on the samples were carried out on, AB SCIEX TOF/TOF 5800, (ABSCIEX), Voyager DE-STR MALDI-TOF MS instrument (Applied Biosystems) and SYNAPT HDMS (on MALDI-TOF mode) Mass Spectrometry Systems (Waters). The former is equipped with a 337 nm nitrogen laser, 2.0 m long TOF tube and a sample target plate with 100 wells. The accelerating voltage was set to 20 kV in the positive ion mode and the laser intensity was adjusted to obtain better spectral resolution and signal-to-noise ratio. All mass spectral analysis was carried out in reflectron mode with 100 shots/spectrum and a delay time of 190 ns. Data analysis was performed using Data Explorer software.

The SYNAPT HDMS MALDI QTOF MS system was equipped with 8 kDa Quad operated in V mode for increased sensitivity over a mass range of m/z 0.1-5000 and m/z 1-10000 depending on the sample requirements in positive polarity. A 355 nm Nd:YAG laser is fixed to the instrument and the laser firing rate was kept at 200 Hz. The data is evaluated using MassLynx software after the data acquisition was done. Calibration performed using DIOS small molecule mix provided by Waters, part no: 186002819.

Sample Preparation for LDI-MS

Sample preparation protocol using N-acyl homoserine lactones and synthetic peptides as an example is as follows: 2 mg/ml solution of pure N-acyl homoserine lactones with structures and masses of lithiated adducts (m/z 178.1055, 206.1368, 220.1161, 220.1525, 234.1681, 262.1994, 290.2307, 318.2620 respectively for 8 analytes) as shown in FIG. 3 were used for all mass spectrometry studies. Synthetic peptides used as standards for mass spectrometry such as Bradykinin 1-7, Angiotensin II, P14R and ACTH 18-39 fragments (m/z 757.4075, 1056.5511, 1533.866, 2465.2067 of protonated adducts respectively) were used.

SBA-15 was dispersed in methanol or acetonitrile as described above. For this specific example of N-acyl homoserine lactone detection from a test mixture containing peptides, the test mixture prepared as described above was split into two fractions. One fraction was used for MALDI analysis using standard protocols and matrices. The second fraction was used for the demonstration of the selective detection using SBA-15 as follows: For a typical LDI-MS study using SBA-15, known volumes of the SBA-15 are placed on the stainless steel target plate, allowed to air dry and followed by placing the test mixture/sample mixture. The SBA-15 particles can also be deposited on top of the sample mixture or the sample can also be sandwiched between layers of the SBA-15 particles or pre-mixed along with the analyte mixture. SBA-15 can also be deposited directly onto the sample sticking to any surfaces, for e.g., tissue sections etc.

Example 4

Figure 4:
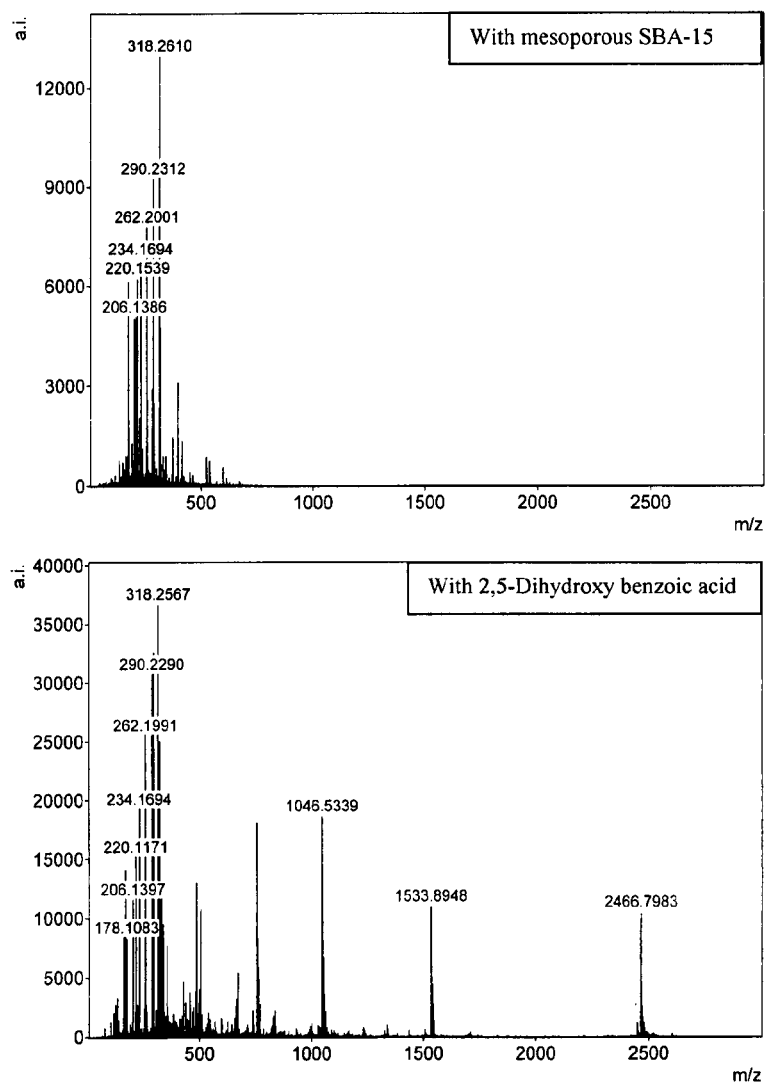
FIG. 4. LDI MS of a mixture of synthetic peptide standards and N-Acyl Homoserine lactone molecules from SBA-15 particles (a) compared to LDI MS using a conventional MALDI matrix, 2,5-dihydroxybenzoic acid (b). Peptide peaks for Bradykinin 1-7, Angiotensin II, P14R and ACTH 18-39 [m/z 757.4075, 1056.5511, 1533.866, 2465.2067 respectively] fragments that can clearly be detected in the MALDI MS are missing from the MS using SBA-15 particles. However, homoserine lactones that are lower in MW can be detected using both and thus SBA-15 is selectively enabling the low MW desorption and ionization. Exact m/z of the homoserine lactones given in FIG. 3.
Figure 5:
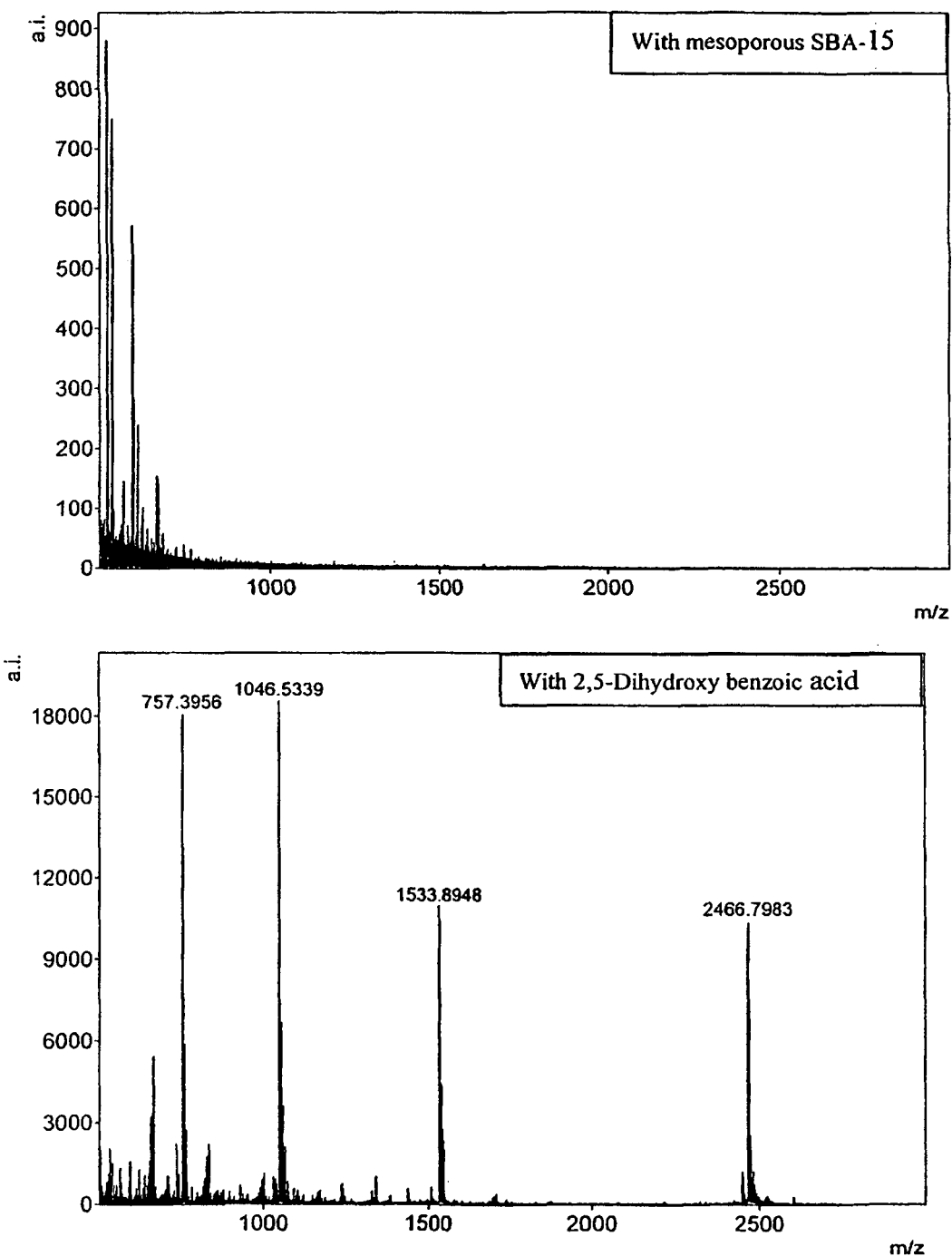
FIG. 5. Highlighted portion of mass region between 500-3000 from FIG. 4 showing clear identification only with MALDI (2,5-dihydroxy benzoic acid) and not with SBA-15 particles.
Figure 6:
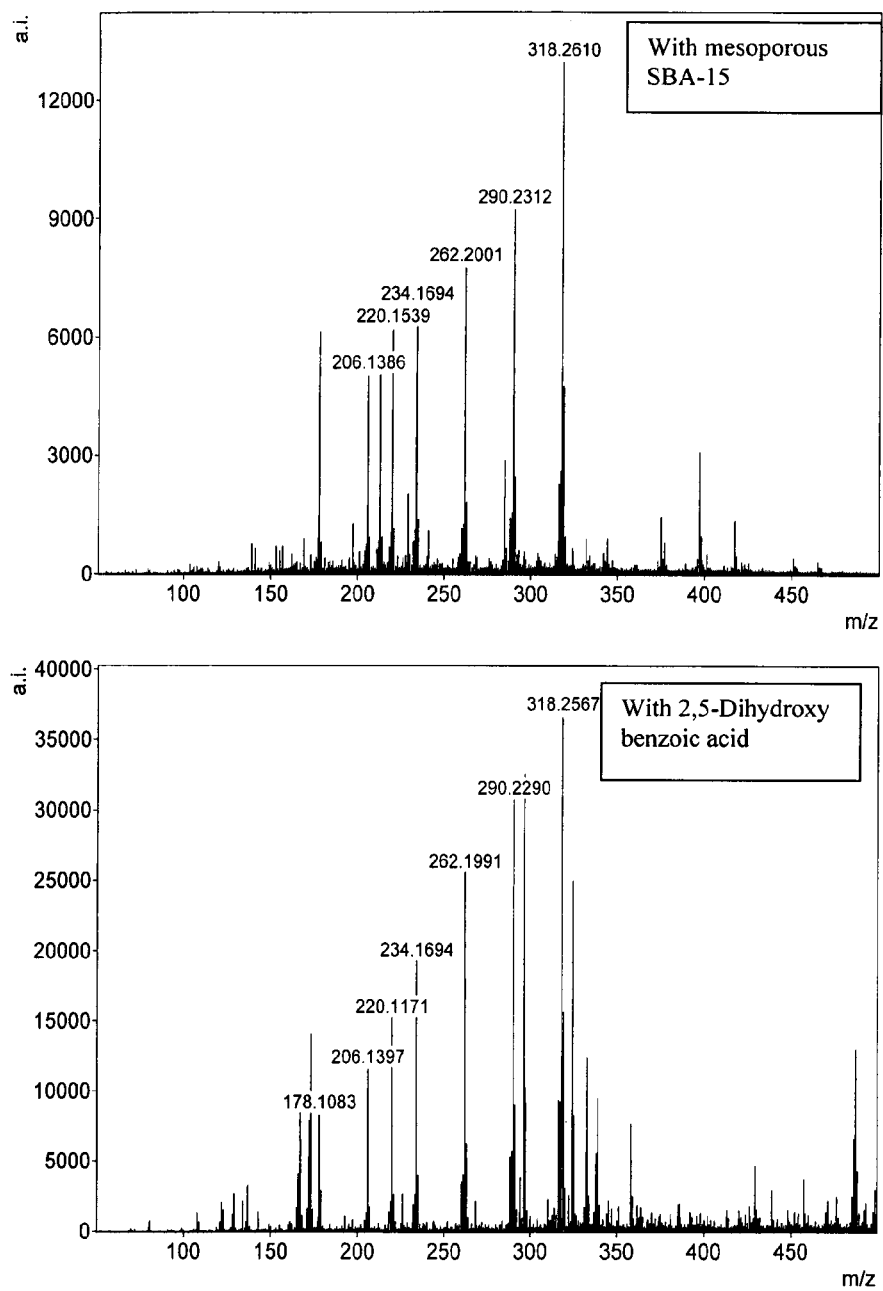
FIG. 6. Highlighted portion of mass region between m/z 50-500 from FIG. 4 showing clear identification of the test low MW analytes (i.e. N-Acyl homoserine lactones).
Figure 7:
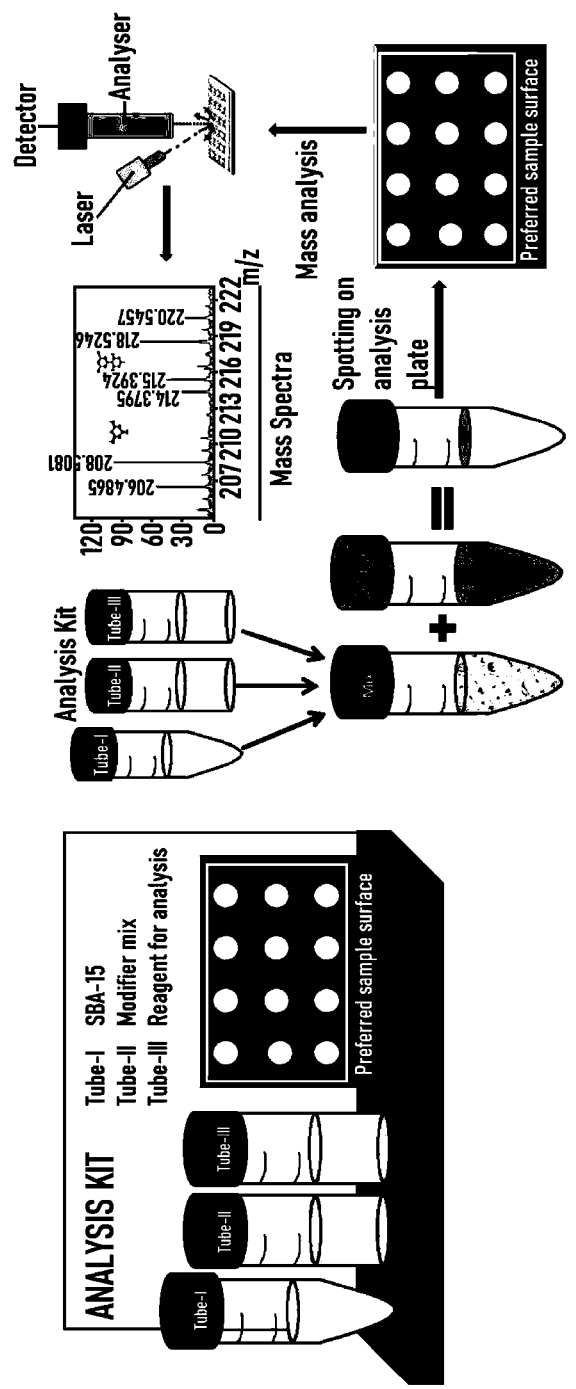
FIG. 7. Schematic description of a kit (left frame). In the right frame, a possible mode of usage of the kit with the steps involved in selective detection of small molecules is described.

Selective Detection of N-Acyl Homoserine Lactones and Exclusion of Peptides Using SBA-15 Particles FIGS. 1 and 2 clearly provide the surface characteristics of the mesoporous SBA-15 particles. The transmission electron microscopy image clearly brings out the porous nature of the material whereas the p-XRD patterns highlight the ordered nature of the pores. FIG. 3 shows the structures of a class of molecules called N-acyl homoserine lactones that are implicated in bacterial biofilm formation that have been used for demonstrating the utility of SBA-15 particles in selective detection. In a phenomenon called 'quorum sensing' bacterial biofilm growth is influenced by these low molecular weight analytes that are sensed by bacterial cells. A test mixture containing lithiated N-acyl homoserine lactones as shown in FIG. 3 (m/z 178.1055, 206.1368, 220.1161, 220.1525, 234.1681, 262.1994, 290.2307, 318.2620 respectively for 8 analytes) together with synthetic peptides Bradykinin 1-7, Angiotensin II, P14R and ACTH 18-39 fragments (m/z 757.4075, 1056.5511, 1533.866, 2465.2067 respectively) was analyzed using both 2,5-dihydroxybenzoic acid (DHB) and SBA-15 assisted LDI MS. Peptide peaks for Angiotensin II, Bradykinin 1-7, P14R and ACTH 18-39 fragments that can clearly be detected in the MALDI MS are missing from the MS using SBA-15 particles as seen in FIG. 4. However, homoserine lactones that are lower in MW can be detected using both and thus SBA-15 is selectively enabling the low MW desorption and ionization. FIGS. 5 and 6 show the zoomed in region of low (50-500) and high MW range (500-3000), again, clearly showing the SBA-15 excluding the peptides while enabling the LDI MS of low MW analytes.

Example 5: Detection of Amino Acids

SBA-15 was suspended in methanol (5 mg/mL) in the first tube. Separately, 7.5 mg/mL of lithium chloride was prepared in a second tube. Finally, the amino acid standards and peptides were dissolved in acetonitrile:trifluoroacetic acid (50:50 v/v) in a third tube. All the three of the above solutions were mixed in 1:1:1 ratio and 1 or 2 microliters of this mixture spotted on a steel surface. After drying, the spot was analyzed using LDI MS. For the control experiment, amino acid and peptide sample mixture was spotted using a MALDI matrix of 2, 5-DHB, dried and analyzed using MALDI MS. In the control spectra, both peptides and amino acids are detected. However, using the lithiated SBA-15 suspension, only amino acids were selectively detected [FIG. 8].

Example 6

Figure 11:
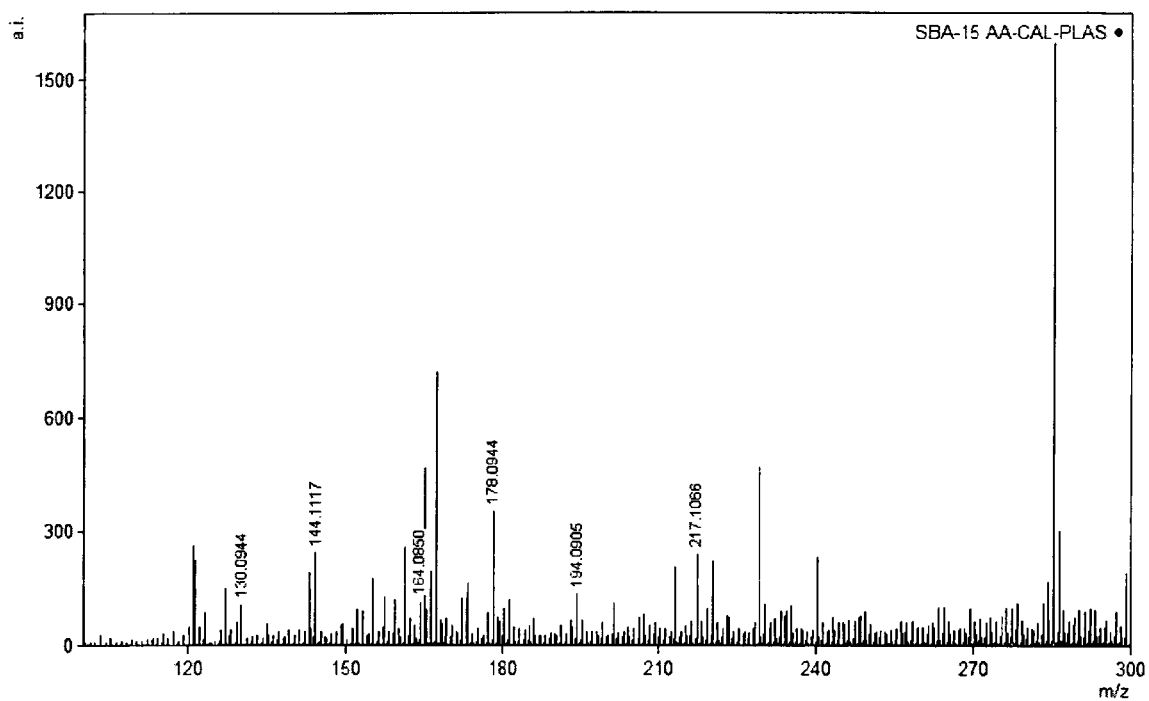
FIG. 11. Schematic representation of selectivity of small molecules from plasma.

For the plasma spiking and selective detection, the following procedure was used: To 100 uL of human plasma, 300 uL of cold methanol (kept at −80 C) was added. The supernatant was collected after centrifugation and used for further studies. To 50 uL of plasma supernatant, 50 uL of analyte mix containing amino acids and standard peptides was added and mixed. 10 uL of this was taken for analysis using MALDI MS (three different 2, 5-DHB, alpha CHCA and CHCA-modified SBA-15) as controls. 10 uL of this solution was mixed with 10 uL of SBA-15 in solution in methanol (5 mg/mL) followed by 10 uL of lithium chloride (7.5 mg/mL). 2 uL of this 1:1:1 (v/v) mixture was then placed on the steel target plates and air dried followed by LDI-MS analysis. As can be seen from the drawing, only the spiked amino acids were selectively detected while the peptides were excluded. In the control MALDI MS using all the three materials, both peptides and amino acids were detected, thus exhibiting no selectivity. Also, in the latter, not all amino acids could be resolved owing to ion suppression and matrix interferences [FIG. 11].

Example 7: Use in a Bioassay for Selective Small Molecule Detection

SBA-15 was implemented in selective detection following a peroxidase assay. Pyrogallol was used as a substrate, which was converted to purpurogallin (a small molecule product) by the enzymatic action of horseradish peroxidase (a high MW protein). The as prepared assay solution was processed as described above using SBA-15 suspension and purpurogallin was selectively detected in the mass spectra.

Other analytes, either from synthetic samples or from biological or other complex samples, having lower or smaller m/z that are similar, somewhat similar or very different in their chemical classes and structures could also reveal the selective nature with respect to the material, method, analysis, mass spectral device, analytical device as a whole or a combination thereof.

REFERENCES

Chen, C.-T. and Y.-C. Chen (2004). "Desorption/ionization mass spectrometry on nanocrystalline titania sol-gel-deposited films." *Rapid Commun. Mass Spectrom.* 18: 1956-1964.

Dattelbaum, A. M., R. K. Hicks, et al. (2008). "Surface assisted laser desorption-ionization mass spectrometry on patterned nanoporous silica thin films." *Microporous and Mesoporous Materials* 114: 193-200.

Go, E. P., J. V. Apon, et al. (2005). "Desorption/Ionization on Silicon Nanowires." *Analytical Chemistry* 77(6): 1641-1646.

Kawasaki, H., T. Yonezawa, et al. (2007). "Platinum Nanoflowers for Surface-Assisted Laser Desorption/Ionization Mass Spectrometry of Biomolecules." *J. Phys. Chem. C* 111: 16278-16283.

Kinumi, T., T. Saisu, et al. (2000). "Matrix-assisted laser desorption/ionization time-of-flight mass spectrometry using an inorganic particle matrix for small molecule analysis." *Journal of Mass Spectrometry* 35: 417-422.

Shen, Z., J. J. Thomas, et al. (2001). "Porous Silicon as a Versatile Platform for Laser Desorption/Ionization Mass Spectrometry." *Analytical Chemistry* 73(3): 612-619.

Siuzdak, G., E.; (US), J. U. Buriak, et al. (2000). Improved desorption/ionization of analytes from porous light-absorbing semiconductor.

Srinivas Iyer, L. A. N. U. and L. A. N. U. Andrew M. Dattelbaum (2005). Sample Desorption/Ionization from Mesoporous Silica, The Regents of the University of California, Los Alamos, N. Mex. (US).

Thomas, J. J., Z. Shen, et al. (2001). "Desorption/ionization on silicon (DIOS): A diverse mass spectrometry platform for protein characterization." *PNAS* 98(9): 4932-4937.

Wei, J., J. M. Buriak, et al. (1999). "Desorption-ionization mass spectrometry on porous silicon." *Nature* 399: 243-246.

Zhao, D., P. Yang, et al. (1998). "Continuous Mesoporous Silica Films with Highly Ordered Large Pore Structures." *Advanced Materials* 10(16): 1380-1385.

We claim:

1. A process for selective detection of molecules of low molecular weight from a sample comprising of low molecular weight molecules and high molecular weight molecules, wherein low molecular weight molecules are defined as those with mass-over-charge (m/z) less than 1000 where z is 1 and high molecular weight molecules are defined as those with m/z is 1000 or greater where z is 1 comprising the steps of:
   (a) preparing a suspension mixture of sample comprising low molecular weight molecules and high molecular weight molecules in a solvent containing chemically unmodified SBA-15 particles along with a charge modifier;
   (b) the molecules in the sample undergo charge modification due to the charge modifier, which is a chemical agent capable of introducing positive or negative charges to both low molecular weight and high molecular weight molecules, but not the SBA-15 or the solvent;
   (c) placing the suspension mixture on a standard MALDI plate and subjecting the mixture to laser desorption ionization mass spectrometry, during which the charge modified and unmodified higher molecular weight molecules as well as the SBA-15 particle aggregates in the mixture are selectively excluded from desorption;
   (d) wherein the selective exclusion of the large molecules and SBA-15 from desorption is due to the nonspecific binding of large molecules on the SBA-15 via physical adsorption to the unmodified SBA-15 particles or ionic or nonionic interactions between the large molecular weight molecules or SBA-15, all or a combination of these factors, thereby precluding them from entering the gas phase and detection;
   (e) wherein the charge modified low molecular weight molecules are selectively desorbed and ionized into the gas phase leading to their exclusive detection and identification in the mixture; and wherein molecules of low molecular weight are detected from the sample comprising low molecular weight molecules and high molecular weight molecules.

2. The process as claimed in claim 1, wherein SBA-15 and solvent are present in a ratio of 5:1 (w/v).

3. The process as claimed in claim 1, wherein said solvent is methanol, acetonitrile or ethyl acetate.

4. The process as claimed in claim 1, wherein the charge modifier is selected from alkali metal salts and is lithium chloride.

5. The process as claimed in claim 1, wherein the ratio of SBA-15 and charge modifier is from 1:1-7:1 (w/v).

6. The process as claimed in claim 4, wherein the sample and SBA-15 is mixed with lithium chloride in methanol.

7. The process as claimed in claim 4, wherein SBA-15 is mixed with lithium chloride in methanol at a ratio of 7:1 (w/v) leading to chemical modification of protonated, sodiated and potassiated adducts of molecules into mono-lithiated adducts; thereby combining the signal intensities of three different adducts into a single lithiated adduct.

8. The process as claimed in claim 1, wherein said sample is a fluid of biological or synthetic origin comprising a mixture of low molecular weight molecules and high molecular weight molecules.

9. The process as claimed in claim 1, for use in clinical diagnostics, forensics, dope and narcotic analysis, environmental analysis, microbial community and quorum sensing molecules analyses pesticide analysis, food analysis, industrial fermentation, active pharmaceutical ingredient (API) or drug discovery or for high throughput mass spectrometry research use and practice wherein the sample comprises a mixture of low molecular weight molecules and higher molecular weight molecules as defined in claim 1.

10. The process as claimed in claim 1, wherein the molecules detected include bacterial quorum sensing molecules, amino acids, synthetic or modified small molecules, lipids, fatty acids and their derivatives, therapeutic, pharmaceutical and drug molecules, metabolites, food, pesticide and environmental samples.

11. The method according to claim 1, for the detection of amino acids from a sample wherein the amino acids are molecules of low molecular weight and proteins and/or peptides are molecules of higher molecular weight.

12. The process as claimed in claim 1, wherein the SBA-15 particles are employed as particles as powder or suspension in reagents or on a surface or as a free standing film or as a part of a device such as a chromatographic or mass spectrometric surface or device.

13. The process as claimed in claim 1 wherein the SBA-15, the charge modifier and laser desorption ionization thereof enables the transition of the molecules in the sample into gas or gaseous phase followed by selective mass analysis.

* * * * *